(12) United States Patent
Fontana et al.

(10) Patent No.: US 9,670,169 B2
(45) Date of Patent: Jun. 6, 2017

(54) PROCESS FOR THE PREPARATION OF EFAVIRENZ USING KETON SOLVENTS

(71) Applicant: F.I.S.—FABBRICA ITALIANA SINTETICI S.P.A., Montecchio Maggiore (VI) (IT)

(72) Inventors: Francesco Fontana, Longone al Segrino (IT); Pierluigi Padovan, Montecchio Maggiore (IT); Marco Prebianca, Muzzolon di Cornedo vicentino (IT)

(73) Assignee: F.I.S.—FABRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 15/116,332

(22) PCT Filed: May 7, 2015

(86) PCT No.: PCT/EP2015/060048
§ 371 (c)(1),
(2) Date: Aug. 3, 2016

(87) PCT Pub. No.: WO2015/173106
PCT Pub. Date: Nov. 19, 2015

(65) Prior Publication Data
US 2017/0008861 A1    Jan. 12, 2017

(30) Foreign Application Priority Data
May 12, 2014  (EP) .................................... 14167938

(51) Int. Cl.
*C07D 265/18*    (2006.01)

(52) U.S. Cl.
CPC .................................. *C07D 265/18* (2013.01)

(58) Field of Classification Search
CPC ..................................................... C07D 265/18
See application file for complete search history.

(56) References Cited

FOREIGN PATENT DOCUMENTS

| EP | 2384324 B1 | | 4/2014 | | |
|---|---|---|---|---|---|
| WO | 9827073 A1 | | 6/1998 | | |
| WO | 2010032259 A2 | | 3/2010 | | |
| WO | WO 2010/032259 | * | 3/2010 | ........... | C07D 265/18 |
| WO | 2010085978 A1 | | 8/2010 | | |
| WO | 2012048886 A1 | | 4/2012 | | |
| WO | WO 2012/048884 | * | 4/2012 | ........... | C07D 265/18 |

OTHER PUBLICATIONS

Smith, M. B. Organic Synthesis, McGraw-Hill, Inc., 1994, Chapter 1.*
International Search Report and Written Opinion for International Application No. PCT/EP2015/060048 ( Jun. 12, 2015) (13 pages).

* cited by examiner

*Primary Examiner* — Erich A Leeser
(74) *Attorney, Agent, or Firm* — Lucas & Mercanti, LLP

(57) ABSTRACT

An improved process for the preparation of Efavirenz which avoids the distillations of the solvents is provided.

11 Claims, No Drawings

PROCESS FOR THE PREPARATION OF EFAVIRENZ USING KETON SOLVENTS

CROSS-REFERENCE TO RELATED APPLICATIONS

This application is a 371 of PCT/EP2015/060048 filed May 7, 2015, which claims the benefit of European Patent Application No. 14167938.1, filed May 12, 2014.

TECHNICAL FIELD

The present invention refers to an improved process for the preparation of the active pharmaceutical ingredient named Efavirez.

BACKGROUND ART

Efavirenz is a well known non-nucleoside reverse transcriptase inhibitor (NNRTI) and is used in the highly active antiretroviral therapy (HAART) for the treatment of a human immunodeficiency virus (HIV) type 1 and is on the market for this use since 1998.

Efavirenz is chemically described as (S)-6-chloro-(cyclopropylethynyl)-1,4-dihydro-4-(trifluoromethyl)-2H-3,1-benzoxazin-2-one and has formula (I):

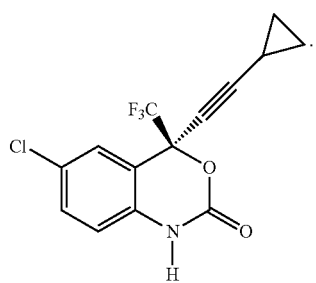

(I)

Several processes are known in the prior art to produce this active substance starting from the intermediate of formula (II):

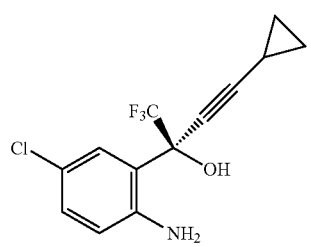

(II)

This intermediate, (2S)-2-(2-amino-5-chlorophenyl)-4-cyclopropyl-1,1,1-trifluorobut-3-yn-2-ol, as a free base, is reacted with a chloroformate derivative under basic conditions to give, after from 1 to 6 hours of reaction, an alkyl carbamate intermediate (reaction of the amine moiety of intermediate (II) with the chloroformate derivative) that is then cyclized to yield Efavirenz.

Although this kind of reactions allows to obtain Efavirenz with an acceptable impurities profile, it has some disadvantages due to the length of the reaction time and/or the quite complicate work-up, as the alkyl carbamate intermediate must be isolated or the reaction mixture must be at least separated and concentrated before undergoing the cyclization step.

The one-pot synthesis starting from the compound of formula (II) as free base has been thus developed submitting such compound to a phosgenation reaction in an appropriate organic solvent or solvent mixtures.

In particular, the compound of formula (II) has been cyclized thus providing Efavirenz by means of phosgene in THF (see Journal of Organic Chemistry 1998, vol.63 pag. 8536-8543 (1998)) or using trichloromethylchloroformate (Diphosgene) in mixtures of THF and heptanes (see the patent publication WO2010/085978).

The main drawbacks of these processes is that the tetrahydrofuran solvent can react with the hydrochloric acid developed by the phosgenation reaction thus providing the by-product 4-choro-1-butanol and related addition products with the compound of formula (II), which are classified as a mutagenic substances.

It is therefore very important to avoid completely the formation of the impurity 4-chloro-1-butanol and related impurities which could be formed at ppm level either working at acid or a neutral or basic/buffered pH, in this last two cases due to the acid microenvironment generated by the release of hydrochloric acid during the phosgenation reaction.

The patent EP2384324B1 already discloses a method for removing also traces of the impurity 4-chloro-1-butanol, nevertheless it would be better to solve this problem in another way, i.e. avoiding the formation of these impurities, instead than to remove them.

The publication WO2010/032259 in example 2 discloses a process for the preparation of Efavirenz from the compound of formula (II) in 1 volume of acetone and 2 volumes of aq. sodium bicarbonate, adding triphosgene dissolved in 2 volumes of acetone. Differently from the prior art methods, Efavirenz was isolated by addition of water that promoted the precipitation of Efavirenz and then by filtration of the suspension. The declared purity of Efavirenz is 99.84%, nevertheless, repeating this experiment exactly in the same conditions (see example 6) and analyzing the product according to the analytical method used to analyze all the Efavirenz samples of the present invention as described in example 7 of the present application, the Efavirenz so prepared shows HPLC purity 99.21% a/a and HPLC assay 96.62% wt/wt, only.

In example 5 of WO2010/032259 the phosgenation reaction is carried out in propionitrile achieving a level of purity of 99.66%, lower than that achieved by the Efavirenz of example 1, according to that applicant.

The methods disclosed the examples 2 and 5 of WO2010/032259 have the drawback that the Efavirenz thus prepared have a relatively low chemical purity, i.e. lower than 99.80% HPLC a/a% and lower than 98.0% of HPLC assay wt/wt.

The publication WO2010/085978 discloses a method for the preparation of Efavirenz wherein the compound of formula (II) in a mixture of 2.6 volumes of THF, 2.6 volumes of heptanes and 7 volumes of aq. sodium bicarbonate is converted to Efavirenz with diphosgene. Efavirenz was obtained in 93% molar yield and shows HPLC purity higher than 99.8%. The main drawback of this method is that to isolate Efavirenz is necessary to distill many times the organic phase composed by Efavirenz dissolved in heptanes and THF, to remove the THF (until the THF content was less than 0.1% (GC)) so that Efavirenz polymorphic form 1 can be produced.

Other drawbacks of said method are:
the potential presence of traces of impurity 4-chloro-1-butanol and related impurity with the compound (II), due to the presence of THF;
the relatively high volumes of solvents used to perform the reaction, with negative impact on the productivity of the process.

The application WO2012/048886 discloses a method for the preparation of Efavirenz from the compound of formula (II) solving the above problem related to the impurity 4-chloro-1-butanol by using mixtures of esters solvent, e.g. acetates, with heptanes, thus substituting the THF. Moreover, these particular solvent mixtures provides Efavirenz with high yields and improved purity over many of the previous known methods (but at the same levels of the process disclosed in WO2010/085978). Finally, the phosgenation reaction is carried out in relatively low volumes of solvents with a positive impact on the productivity of the process.

The main drawback of this last improved process is that, as other previous method for the preparation of Efavirenz by phosgention of the compound (II), such as that disclosed in WO2010/085978, after the end of the reaction and during the work up, it is necessary to perform the distillations of the organic solvents to isolate the product (see examples 6-11 wherein distillations where carried out to achieve a content of ethyl acetate comprised between 3 and 7 w/w%).

In particulars, in the methods disclosed in both the publications WO2010/085978 and WO2012/048886, after a first distillation of the organic phase, further additions of fresh heptanes followed by distillations were carried out to remove the other co-solvent being respectively THF or acetates.

On industrial scale, the distillation of organic phases requires a very long time, additional huge amounts of fresh heptanes and represents an actual bottom-neck for the large industrial production of Efavirenz. Furthermore, it impacts directly both on the productivity of the process and on the full cost of the product.

SUMMARY OF INVENTION

The problem addressed by the present invention is therefore that of providing an improved process for the preparation of Efavirenz, with increased productivity and lower costs of the product, which, in particular, allows to avoid the step of distillation of the organic phase, keeping at the same time:
very high chemical purity of the product, i.e. higher than 99.80% HPLC a/a% and higher than 98.0% HPLC assay wt/wt.
high molar yield,
low volumes of solvents used during the phosgenation reaction,
and avoiding the formation of genotoxic impurities, such as e.g. 4-chloro-1-butanol and related impurities.

This problem is solved by a process for the preparation of Efavirenz as outlined in the annexed claims, whose definitions are integral part of the present description.

Further features and advantages of the process according to the invention will result from the description hereafter reported of examples of realization of the invention.

DESCRIPTION OF EMBODIMENTS

The object of the present invention is a process for the preparation of Efavirenz, (4S)-6-chloro-4-(cyclopropylethynyl)-4-(trifluoromethyl)-1,4-dihydro-2H-3,1-benzoxazin-2-one, of formula (I):

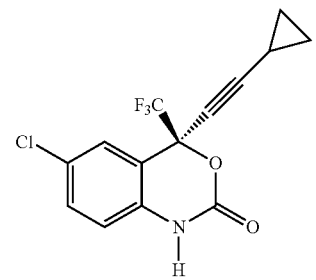

comprising the phosgenation reaction of the compound of formula (II) or salt thereof:

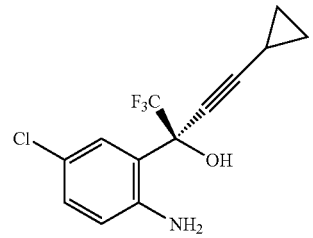

with a phosgenating agent and the reaction is performed in a biphasic system consisting in an aqueous basic or neutral phase and an organic phase, characterized in that the organic phase comprises a $C_{5-8}$ linear or branched or cyclic aliphatic solvent or mixtures thereof and at least 20% by volume of a $C_{3-5}$ ketone solvent.

It has now been surprisingly found that by reacting the intermediate (II) with a phosgenating agent, in a biphasic system, wherein the organic phase comprises a $C_{5-8}$ linear or branched or cyclic aliphatic solvent or mixtures thereof and at least 20% by volume of a $C_{3-5}$ ketone solvent, it is possible to prepare Efavirenz with high molar yields, very high chemical purity, avoiding the distillations of the solvents to isolate Efavirenz and, in general, increasing the productivity, thus reducing the cost of Efavirenz.

The presence of the $C_{3-5}$ ketone solvent provides indeed two effects, the first one being the reduction of the volumes of solvents used to carry out the phosgenation reaction, so that it is possible to perform such reaction also in 2.5 to 4.0 volumes of organic solvent, hence, considering the same reactor capacity, the batch size of production can be increased.

The second effect is that it is possible to remove almost completely the $C_{3-5}$ ketone solvent without to perform any solvent distillation. In the previous methods such as for example those of WO2012/048886 and WO2010/085978, during the work up, the distillations of the organic phase, typically constituted by heptanes, were carried out with the aim to remove almost completely the co-solvent used during the reaction, co-solvent whose presence was absolutely necessary to solubilize either Efavirenz or the compound of formula (II). Thus, it was typically necessary to conduct long distillations and replacements of the organic phase, in particular, replacing each time part of it with fresh heptanes so that the residual co-solvent, often being THF, reached the limit of below 2% (v/v). Complying with such limit it allows indeed the preparation of Efavirenz having crystalline form I and with high yields.

Although during the work-up there are two phase, one aqueous and one organic made of a $C_{5-8}$ linear or branched or cyclic aliphatic solvent, typically being a mixture of heptanes, the $C_{3-5}$ ketone solvent is quickly removed from the organic phase by few washings of the organic phase with water, so that the removal by distillation can be avoided and then the productivity can be greatly improved.

Other organic solvents, such as for examples acetates or ethers remain instead into the organic phase, i.e. they are not removed by washing with water, so that it is mandatorily necessary to perform some distillations to remove said solvents form the aliphatic solvent of the organic phase. Moreover, since the organic phase comprises aliphatic solvents, differently from the method disclosed in WO2010/032259 wherein were not used aliphatic solvents, the addition of water does not promote the precipitation of Efavirenz so that it not possible to isolate Efavirenz by precipitation thus avoiding the distillations. At the same time, the method disclosed in WO2010/032259 wherein Efavirenz is precipitate by water does not allow to achieve the desirable level of chemical purity of the product being HPLC purity higher than 99.80% a/a% and HPLC assay higher than 98.0% wt/wt, as achieved by the methods of WO2012/048886 and WO2010/085978. Both the effects said above indeed impact on the productivity, therefore allowing to produce Efavirenz having crystalline form I, at lower costs.

The phosgenation agent can be chosen between phosgene, dichloromethylcloroformate (Diphosgene), triphosgene, Carbonyldiimidazole, etc.

The biphasic system is a reaction system comprising two immiscible phases. In the present process, one phase is an aqueous basic phase and the other is an organic phase.

The aqueous basic phase is an aqueous solution comprising one or more inorganic or organic bases. Inorganic bases can be selected between $Na_2CO_3$, $K_2CO_3$, $NaHCO_3$, $KHCO_3$, etc., being preferred $NaHCO_3$.

The $C_{5-8}$ linear or branched or cyclic aliphatic solvent or mixtures thereof can be selected from pentane, hexane, heptane or octane, cyclohexane, cycloctane, cyclopentane, etc., their isomers and mixtures thereof.

Mixture of heptanes (also named heptanes) is a preferred aliphatic solvent for the process of the present invention.

The organic phase of the process of the present invention comprises at least 20% by volume of a $C_{3-5}$ ketone solvent. This means that this organic phase comprises from 20% to 99.9% of a $C_{3-5}$ ketone. The value 20% by volume means an organic phase made with 1 part in volume of $C_{3-5}$ ketone and 4 parts in volume of $C_{5-8}$ linear or branched or cyclic aliphatic solvent. For example 1 mL of acetone and 4 ml of heptanes.

An organic phase having 50% by volume of a $C_{3-5}$ ketone solvent means, for example, 1 litre of $C_{3-5}$ ketone solvent and 1 litre of aliphatic solvent.

The $C_{3-5}$ ketone solvent is a ketone solvent which can be linear, ramified, or cyclic and is chosen in the group comprising acetone, methylethylketone, methylisopropylketone, 2-pentanone, 3-pentanone, cyclopentanone, etc.

According to a more preferred embodiment the process of the present invention is carried out with an organic phase which comprises a $C_{3-5}$ ketone solvent in the range from 20% to 80% by volume.

According to a more preferred embodiment the process of the present invention is carried out with an organic phase which comprises a $C_{3-5}$ ketone solvent in the range from 30% to 70% by volume.

According to an again more preferred embodiment, the process of the present invention is carried out with an organic phase which comprises a $C_{3-5}$ ketone solvent in the range from 40% to 60% by volume.

According to a preferred embodiment, the process of the present invention is carried out with a volume of the organic phase from 2.5 to 4.0 volumes in respect to the compound of formula (II). This means that, for example, for 1 Kg of compound of formula (II), from 2.5 to 4.0 litres of organic phase are used.

More preferably, the process is carried out with a volume of the organic phase from 3.0 to 3.5 volumes in respect to the compound of formula (II).

According to a preferred embodiment, the process of the present invention is carried out with an organic phase which comprises a $C_{3-5}$ ketone solvent in the range from 20% to 80% by volume and the volume of the organic phase is from 2.5 to 4.0 volumes in respect to the compound of formula (II).

According to a preferred embodiment, the process of the present invention is carried out with an organic phase which comprises a $C_{3-5}$ ketone solvent in the range from 30% to 70% by volume and the volume of the organic phase is from 2.5 to 4.0 volumes in respect to the compound of formula (II).

More preferably, according to a more preferred embodiment, the process of the present invention is carried out with an organic phase which comprises a $C_{3-5}$ ketone solvent in the range from 40% to 60% by volume and the volume of the organic phase is from 2.5 to 4.0 volumes in respect to the compound of formula (II).

According to an again more preferred embodiment, the process of the present invention is carried out with an organic phase which comprises a $C_{3-5}$ ketone solvent in the range from 40% to 60% by volume and the volume of the organic phase is from 3.0 to 3.5 volumes in respect to the compound of formula (II).

According to an again more preferred embodiment, the process of the present invention is carried out with an organic phase which comprises a $C_{3-5}$ ketone solvent in amount of 50% by volume and the volume of the organic phase is from 3.0 to 3.5 volumes in respect to the compound of formula (II).

According to the best embodiment, the process of the present invention is carried out with an organic phase which comprises a $C_{3-5}$ ketone solvent in amount of 50% by volume and the volume of the organic phase is 3.0 volumes in respect to the compound of formula (II).

The process of the present invention can be carried out with the compound of formula (II) as free base or with a salt thereof, being preferred the salt of the compound of formula (II) having formula (II-MSA):

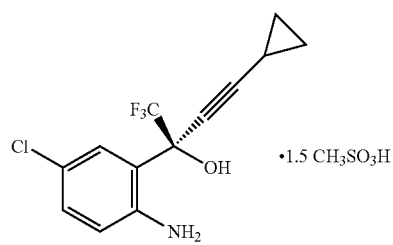 [SMILES: Nc1ccc(Cl)cc1[C@@](O)(C#CC1CC1)C(F)(F)F]

According to a preferred embodiment, the aqueous basic phase comprises $NaHCO_3$.

According to a preferred embodiment of the process of the present invention, the $C_{3-5}$ ketone solvent is acetone or methylethylketone, being more preferred methylethylketone.

According to a preferred embodiment of the process of the present invention, the aliphatic solvent is a mixture of heptanes.

According to a preferred embodiment of the process of the present invention, the $C_{3-5}$ ketone solvent is methylethylketone and the aliphatic solvent is a mixture of heptanes.

More preferably, according to a more preferred embodiment, the process of the present invention is carried out with an organic phase which comprises a methylethylketone in the range from 40% to 60% by volume, the rest being heptanes, and the volume of the organic phase is from 2.5 to 4.0 volumes in respect to the compound of formula (II).

More preferably, according to an again more preferred embodiment, the process of the present invention is carried out with an organic phase which comprises methylethylketone in the range from 40% to 60% by volume, the rest being heptanes, and the volume of the organic phase is from 3.0 to 3.5 volumes in respect to the compound of formula (II).

According to an again more preferred embodiment, the process of the present invention is carried out with an organic phase which comprises methylethylketone in amount of 50% by volume and 50% of heptanes and the volume of the organic phase is from 3.0 to 3.5 volumes in respect to the compound of formula (II).

According to the best embodiment, the process of the present invention is carried out with an organic phase which comprises methylethylketone in amount of 50% by volume and 50% of heptanes and the volume of the organic phase is 3.0 volumes in respect to the compound of formula (II), i.e. 1.5 volumes of methyletylketone and 1.5 volumes of heptanes.

After the quenching of the reaction and the phase separation, the organic phase is washed from 3 to 5 times with water, with an amount of water comprised between 0.5 and 5 volumes referred to the compound of formula (II), preferably between 1 and 3 volumes.

Preferably, the organic phase is washed from 3 to 5 times with about 1.5 volumes of water.

More preferably, the organic phase is washed 3 times with about 1.5 volumes of water.

After the quenching of the reaction and the phase separation, the washings of the organic phase with water are carried out at a temperature comprised between 40° C. and 80° C., preferably at a temperature comprised between 40° C. and 50° C.

According to a preferred embodiment, the organic phase can be washed 3 times with 1.5 volumes of water referred to the compound of formula (II).

According to a preferred embodiment, the organic phase can be washed from 3 to 5 times with water at 40-50° C.

According to a more preferred embodiment, the organic phase can be washed 3 times at 40-50° C. with 1.5 volumes of water referred to the compound of formula (II).

Optionally, after the completion of the washings of the organic phase, less or about 10% of the organic phase can be distilled with the aim of removing the residual water. In this case, the distillation can be carried out at a temperature comprised between 50° C. and 80° C. Said distillation is however not essential for the process of the invention since the removal of the ketone solvent is already effectively carried out by washings the organic phase with water.

Therefore, a $C_{3-5}$ ketone solvent can be therefore used as solvent for the phosgenation reaction of the compound of formula (II) or salt thereof:

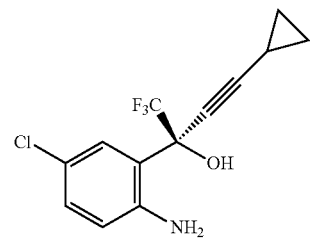

to provide Efavirenz of formula (I), being methyethylketone the preferred solvent.

Therefore, an organic phase comprising a $C_{5-8}$ linear or branched or cyclic aliphatic solvent or mixtures thereof and at least 20% by volume of a $C_{3-5}$ ketone solvent can be therefore used as solvent for the phosgenation reaction of the compound of formula (II) or salt thereof:

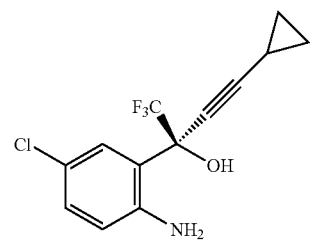

to provide Efavirenz of formula (I).

According to a referred embodiment, the methyethylketone is the preferred solvent for said organic phase.

According to a more preferred embodiment, the mixture methyethylketone and heptanes is the preferred organic phase.

The skilled person can appreciate that the process of the present invention allows to avoid the genotoxic degradation products deriving from THF, allows to increase the batch size and allows a very fast preparation of Efavirenz since distillations of the solvents are avoided, thus reducing the cycling time, and thus well increasing the productivity and, finally, reducing the industrial cost of Efavirenz production.

Indeed, in comparison with the process for the preparation of Efavirenz disclosed by the same applicant of the present application in WO2010/085978A1 based on mixtures of THF and heptanes, the process of the invention wherein the organic phase comprises a $C_{5-8}$ linear or branched or cyclic aliphatic solvent or mixtures thereof and at least 20% by volume of a $C_{3-5}$ ketone solvent allows a reduction of the organic solvent to be distilled of an amount of 55%, thus saving the costs of the solvents. Moreover, avoiding the distillation step, the cycling time has been largely reduced so that productivity is increased, while the final price of Efavirenz is consequently consistently reduced.

EXPERIMENTAL SECTION

The purity HPLC a/a % and Assay HPLC wt/wt % of Efavirenz prepared according to the following experiments have been determined for all the samples by the HPLC method described in example 7 and abbreviated USP1.

The starting material compound of formula (II) being (2S)-2-(2-amino-5-chlorophenyl)-4-cyclopropyl-1,1,1-trifluorobut-3-yn-2-ol as free base used for the experiments from experiment 3 to experiment 6 is always the same, i.e. material from a lot having purity 99.8% HPLC A/A% and 99.86% Assay HPLC wt/wt %.

Example 1

Procedure for the synthesis of efavirenz of formula (I)—exemplificative of the invention.

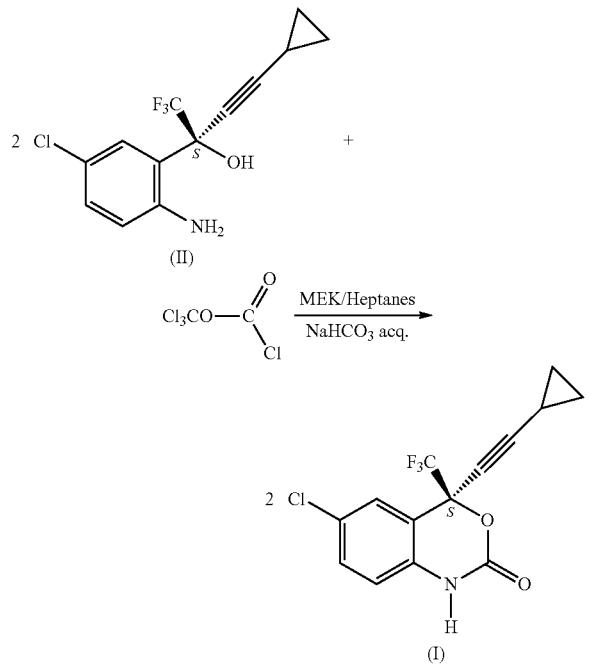

30.0 g of (2S)-2-(2-amino-5-chlorophenyl)-4-cyclopropyl-1,1,1-trifluorobut-3-yn-2-ol as free base (prepared according to the known methods of literature) were charged in a jacketed reactor. 45 mL (1.5 vol.) of methylethylketone and 45 mL of heptane mixture of isomers (1.5 vol.) were added followed by a cloudy solution of 23.6 g (2.71 eq.) of sodium bicarbonate and 180 mL (6 vol.) of purified water. The mixture was cooled at 0-10° C. 12.4 g (0.61 eq.) of trichloromethylchloroformate were rapidly added keeping the temperature between 0° C. and 20° C. The mixture was stirred at 0-20° C. for at least 30 min., then the conversion was checked by HPLC (compound (II) <0.5%). 3.2 mL (0.11 vol.) of aqueous ammonia at 30% were then added keeping the temperature below 25° C. The mixture was stirred at 15-25 ° C. for 30 min and then the pH checked (>8). The clear biphasic mixture was decanted at 25-35° C. for 15-30 min. and the layer were separated. The organic layer was added with 120 mL (4 vol.) of heptanes and with 45 mL (1.5 vol) of purified water. The mixture was heated at 40-50° C. for 30 minutes, then the phases are separated at that temperature. The organic layer was washed again 4 times at 40-50° C. with 45 mL of purified water (1.5 vol), each time stirring for 30 minutes and then separating the phases. At the end of the last phase separation, the product tends to crystallize from the organic phase. 312 mL of heptanes (i.e. heptanes isomers) (10.4 vol.) are then added and the suspension was heated at 75° C. under stirring until complete dissolution. The mixture has then a content of methylethylketone lower than 2.0% v/v.

A cooling ramp was then started following the following steps:

| Step | Temperature | Time | Stirring speed | Note |
|---|---|---|---|---|
| 1 | From 75 to 52° C. | 1 h | 100-200 rpm | |
| 2* | From 52 to 42° C. | 2 h | 100-200 rpm | Seeding (optional) |
| 3 | From 42 to −20° C. | 2 h | 300-500 rpm | |
| 4 | −20° C. | At least 2 h | 200-400 rpm | |

Seeding with Efavirenz form I was performed if spontaneous precipitation did not occur at 48-52° C. Once the cooling ramp program was completed the slurry was filtered washing with 68 mL (2.25 vol) of heptanes pre-cooled at −20 ° C. The product was dried in vacuum at 85-90° C. for at least 8 h. 29.6 g of Efavirenz crystalline form I are thus collected for a molar yield of 90.5%.

Example 2

Comparative general procedure for the synthesis of Efavirenz of formula (I)—including the step of distillation of the solvent.

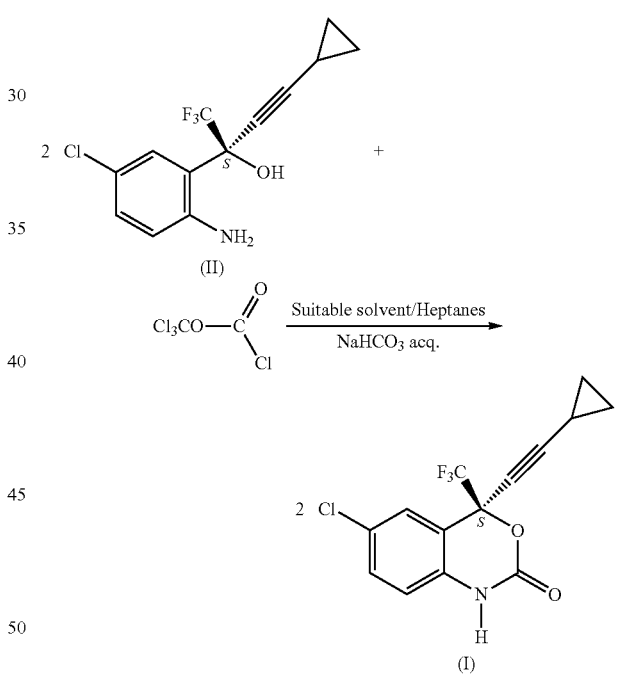

50.0 g of (2S)-2-(2-amino-5-chlorophenyl)-4-cyclopropyl-1,1,1-trifluorobut-3-yn-2-ol as free base were charged in a jacketed reactor. 132 mL (2.63 vol.) of suitable solvent (see second table below) and 132 mL (2.63 vol) of heptanes were added followed by a cloudy solution of 39.3 g (2.71 eq.) sodium bicarbonate and 300 mL (6 vol.) of purified water. The mixture was cooled at 0-10° C. 20.7 g (0.61 eq.) of trichloromethylchloroformate were rapidly added keeping the temperature between 0 and 20° C. The mixture was stirred at 0-20° C. for at least 30 min, then the conversion was checked by HPLC. 5.3 mL (0.11 vol.) of aqueous ammonia at 30% were then added keeping the temperature below 25° C. The mixture was stirred at 15-25° C. for 30 min. and then the pH checked (>8). The clear biphasic mixture was decanted at 25-35° C. and the layer were separated. The organic layer was added with 263 mL (5.27 vol.) of heptanes and washed at 40-50° C. with 75 mL (1.5 vol) of water. The organic layer was washed again twice at 40-50° C. with 75 mL (1.5 vol). The clear organic solution was concentrated in vacuum, keeping the inner temperature at 60-70° C. (jacket temperature 75-80° C.) until a volume of about 300 mL. The mixture was added with 520 mL (10.4 vol.) of heptanes and a sample collected for GC analysis. The mixture was warmed at about 75° C. and stirred until complete dissolution.

Cooling ramp was then started following the following steps:

| Step | Temperature | Time | Stirring speed | Note |
|---|---|---|---|---|
| 1 | From 75 to 52° C. | 1 h | 100-200 rpm | |
| 2* | From 52 to 42° C. | 2 h | 100-200 rpm | Seeding (optional) |
| 3 | From 42 to −20° C. | 2 h | 300-500 rpm | |
| 4 | −20° C. | At least 2 h | 200-400 rpm | |

Seeding with Efavirenz form I was performed if spontaneous precipitation did not occur at 48-52° C. Once the cooling ramp program was completed the slurry was filtered washing with 113 mL (2.25 vol) of heptanes pre-cooled at −20° C. The product was dried in vacuum at 85-90° C. for at least 8 hours.

Yield and quality results are listed in the following table.

| Entry | Suitable Solvent | Starting Material (II) assay | OUTPUT Efavirenz | Molar Yield | Purity HPLC a/a % (USP1) | Assay HPLC wt/wt % (USP1) |
|---|---|---|---|---|---|---|
| 1 | Heptane/MEK (1:1) | 98.6% | 49.3 g | 91.7% | 99.92% | 99.97% |
| 2 | Heptane/THF (1:1) | 98.6% | 46.7 g | 85.3% | 99.93% | 98.14% |
| 3 | Heptane/IPAc (1:1) | 98.6% | 46.0 g | 83.9% | 99.93% | 98.04% |
| 4 | Heptane/EtOAc (1:1) | 99.6% | 49.6 g | 91.0% | 99.95% | 99.61% |

Notes and legend to the table:

INPUT compound of formula (II) free base: 50 g for all the trials.

The molar yield is corrected for SD-573 and Efavirenz assays.

The assay of the starting compound of formula (II) has been determined by NMR via internal standard.

MEK=methylethylketone; THF=tetrahydrofuran; IPAc=isopropylacetate; EtOAc=AcOEt=ethylacetate.

Example 3

Procedure for the synthesis of Efavirenz of formula (I)—experiments with the solvents of the invention.

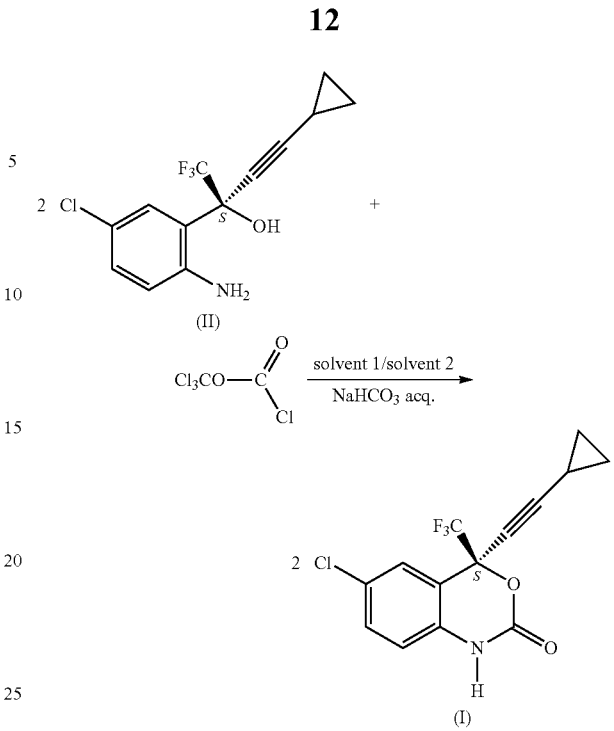

33.3 g of (2S)-2-(2-amino-5-chlorophenyl)-4-cyclopropyl-1,1,1-trifluorobut-3-yn-2-ol as free base (99.8% HPLC NA%; 99.86% Assay HPLC wt/wt %) were charged in a jacketed reactor. 50 mL (1.50 vol.) of solvent 1 (see second table below) and 67 mL (2.00 vol.) of suitable solvent 2 (see second table below) were added followed by a cloudy solution of 26.3 g (2.71 eq.) sodium bicarbonate and 200 mL (6.00 vol.) of purified water. The mixture was cooled at 0-10° C. 14.0 g (0.61 eq.) of trichloromethylchloroformate were rapidly added keeping the temperature between 0 and 20° C. The mixture was stirred at 0-20° C. for at least 30 min, then the conversion was checked by HPLC. 3.6 mL (0.11 vol.) of aqueous ammonia at 30% were then added keeping the temperature below 25° C. The mixture was stirred at 15-25° C. for 30 min. and then the pH checked (>8). The clear biphasic mixture was decanted at 25-35° C. and the layer were separated. The organic layer was added with 134 mL (4.00 vol.) of solvent 2 and washed at 40-50° C. with 50 mL (1.5 vol) of water. The organic layer was washed again twice at 40-50° C. with 50 mL (1.5 vol). The clear organic solution was polish filtered washing with a mixture of 6 mL (0.18 vol) of solvent 1 and 19 mL (0.57 vol) of solvent 2. The mixture was added with 347 mL (10.40 vol.) of solvent 2 and a sample collected for GC analysis. The mixture was warmed at about 75° C. and stirred until complete dissolution.

Cooling ramp was then started following the following steps:

| Step | Temperature | Time | Stirring speed | Note |
|---|---|---|---|---|
| 1 | From 75 to 52° C. | 1 h | 100-200 rpm | |
| 2* | From 52 to 42° C. | 2 h | 100-200 rpm | Seeding (optional) |
| 3 | From 42 to −20° C. | 2 h | 300-500 rpm | |
| 4 | −20° C. | At least 2 h | 200-400 rpm | |

Seeding with Efavirenz form I was performed if spontaneous precipitation did not occur at 48-52° C. Once the cooling ramp program was completed the slurry was filtered washing with 75 mL (2.25 vol) of solvent 2 pre-cooled at −20° C. The product was dried in vacuum at 85-90° C. for at least 8 hours.

Yield (uncorrected) and quality results are listed in the following table.

| Entry | Solvent 1 | Solvent 2 | OUTPUT Efavirenz | Molar Yield | Purity HPLC a/a % (USP1) | Assay HPLC wt/wt % (USP1) |
|---|---|---|---|---|---|---|
| 1 | Acetone | Heptanes | 31.8 g | 87.6% | 99.85% | 99.27% |
| 2 | Methyl isobutyl ketone (MIBK) | Heptanes | 33.5 g | 92.3% | 99.91% | 98.91% |
| 3 | Methyl ethyl ketone (MEK) | Heptanes | 33.7 g | 92.9% | 99.93% | 101.49% |
| 4 | Methyl ethyl ketone (MEK) | Hexanes | 31.5 g | 86.8% | 99.94% | 99.50% |
| 5 | Methyl ethyl ketone (MEK) | Cyclohexane | 26.1 g | 71.9% | 99.93% | 99.12% |

The results in the table above confirm that the invention provide similar results using different combination of aliphatic solvent and ketone solvent mixtures. See entry 1-3 for different ketone solvents screening and see entry 3-5 for different aliphatic solvent screening.

Nevertheless, the mixture where the ketone solvent is methylethylketone are preferred since it provides Efavirenz product with the highest chemical purity, highest assay and highest molar molar yield (see entry 1-3).

Moreover, the mixture where the aliphatic solvent is heptanes are preferred since it provides Efavirenz product with highest assay and highest molar yield (see entry 3-5).

Finally, the mixtures of heptanes and methlyethylketone are preferred since said mixture provided Efavirenz with the highest chemical purity, highest assay and highest molar yield (see entry 3).

Example 4

Procedure for the synthesis of Efavirenz of formula (I)—experiments with different phosgentation agent.

33.3 g of (2S)-2-(2-amino-5-chlorophenyl)-4-cyclopropyl-1,1,1-trifluorobut-3-yn-2-ol as free base (99.8% HPLC NA %; 99.86% Assay HPLC wt/wt %) were charged in a jacketed reactor. 50 mL (1.50 vol.) of methyl ethyl ketone and 67 mL (2.00 vol) of suitable heptanes were added followed by a cloudy solution of 26.3 g (2.71 eq.) sodium bicarbonate and 200 mL (6.00 vol.) of purified water. The mixture was cooled at 0-10° C. 14.0 g (0.61 eq.) bis(trichloromethyl) carbonate (triphosgene, 0.41 eq.) were added portionwise keeping the temperature between 0 and 20° C. The mixture was stirred at 0-20° C. for at least 30 min, then the conversion was checked by HPLC. 3.6 mL (0.11 vol.) of aqueous ammonia at 30% were then added keeping the temperature below 25° C. The mixture was stirred at 15-25° C. for 30 min. and then the pH checked (>8). The clear biphasic mixture was decanted at 25-35 ° C. and the layer were separated. The organic layer was added with 134 mL (4.00 vol.) of heptanes and washed at 40-50° C. with 50 mL (1.5 vol) of water. The organic layer was washed again twice at 40-50° C. with 50 mL (1.5 vol). The clear organic solution was polish filtered washing with a mixture of 6 mL (0.18 vol.) of Methyl ethyl ketone and 19 mL (0.57 vol) of heptanes. The mixture was added with 347 mL (10.40 vol.) of heptanes and a sample collected for GC analysis. The mixture was warmed at about 75° C. and stirred until complete dissolution.

Cooling ramp was then started following the following steps:

| Step | Temperature | Time | Stirring speed | Note |
|---|---|---|---|---|
| 1 | From 75 to 52° C. | 1 h | 100-200 rpm | |
| 2* | From 52 to 42° C. | 2 h | 100-200 rpm | Seeding (optional) |
| 3 | From 42 to −20° C. | 2 h | 300-500 rpm | |
| 4 | −20° C. | At least 2 h | 200-400 rpm | |

Seeding with Efavirenz form I was performed if spontaneous precipitation did not occur at 48-52° C. Once the cooling ramp program was completed the slurry was filtered washing with 75 mL (2.25 vol) of heptanes pre-cooled at −20° C. The product was dried in vacuum at 85-90° C. for at least 8 hours obtaining 33.4 g of product (92.0% yield, HPLC purity 99.89% a/a, HPLC assay 100.05% wt/wt).

This experiment confirms that the process of the invention provides substantially the same results using various phosgenation agents.

Nevertheless, comparing example 4 and entry 5 of experiment 4, diphosgene is a preferred phosgenation agent since it provides higher molar yield and cleaner product.

Example 5

Procedure for the synthesis of Efavirenz of formula (I)—experiments with different ratio of the solvents.

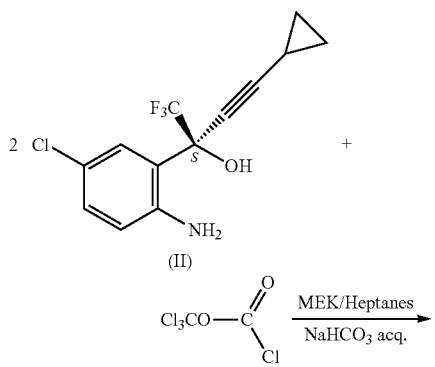

-continued

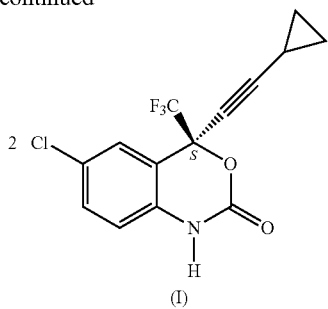

8.5 g of (2S)-2-(2-amino-5-chlorophenyl)-4-cyclopropyl-1,1,1-trifluorobut-3-yn-2-ol as free base (99.8% HPLC NA %; 99.86% Assay HPLC wt/wt %) were charged in a jacketed reactor. Suitable amount of methyl ethyl ketone (MEK) and Heptanes (see second table below) were added followed by a cloudy solution of 6.7 g (2.71 eq.) sodium bicarbonate and 51 mL (6.00 vol.) of purified water. The mixture was cooled at 0-10° C. 3.5 g (0.61 eq.) of trichloromethylchloroformate were rapidly added keeping the temperature between 0 and 20° C. The mixture was stirred at 0-20° C. for at least 30 min, then the conversion was checked by HPLC. 0.9 mL (0.11 vol.) of aqueous ammonia at 30% were then added keeping the temperature below 25° C. The mixture was stirred at 15-25° C. for 30 min. and then the pH checked (>8). The clear biphasic mixture was decanted at 25-35° C. and the layer were separated. The organic layer was added with 34 mL (4.00 vol.) of heptanes and washed at 40-50° C. with 12.8 mL (1.5 vol) of water. The organic layer was washed again twice at 40-50° C. with 12.8 mL (1.5 vol). The clear organic solution was polish filtered washing with a mixture of 1.6 mL (0.18 vol) of methyl ethyl ketone and 4.8 mL (0.57 vol) of heptanes. The mixture was added with 88.5 mL (10.40 vol.) of heptanes and a sample collected for GC analysis. The mixture was warmed at about 75° C. and stirred until complete dissolution.

Cooling ramp was then started following the following steps:

| Step | Temperature | Time | Stirring speed | Note |
|---|---|---|---|---|
| 1 | From 75 to 52° C. | 1 h | 100-200 rpm | |
| 2* | From 52 to 42° C. | 2 h | 100-200 rpm | Seeding (optional) |
| 3 | From 42 to −20° C. | 2 h | 300-500 rpm | |
| 4 | −20° C. | At least 2 h | 200-400 rpm | |

Seeding with Efavirenz form I was performed if spontaneous precipitation did not occur at 48-52° C. Once the cooling ramp program was completed the slurry was filtered washing with 19 mL (2.25 vol) of Heptanes pre-cooled at −20° C. The product was dried in vacuum at 85-90° C. for at least 8 hours.

Yield (uncorrected) and quality results are listed in the following table.

| Entry | Methyl ethyl ketone (MEK) (Vol) | Heptanes (Vol) | OUTPUT Efavirenz | Molar Yield | Purity HPLC a/a % (USP1) | Assay HPLC wt/wt % (USP1) |
|---|---|---|---|---|---|---|
| 1 | 1.64 | 1.81 | 8.4 g | 90.6% | 99.84% | 99.02% |
| 2 | 1.35 | 2.20 | 7.4 g | 79.9% | 99.91% | 99.73% |

Example 6

Procedure for the synthesis of Efavirenz of formula (I)—comparative example of WO2010/032259 Example 2.

10.0 g of (2S)-2-(2-amino-5-chlorophenyl)-4-cyclopropyl-1,1,1-trifluorobut-3-yn-2-ol as free base (99.8% HPLC NA %; 99.86% Assay HPLC wt/wt %) were charged in a jacketed reactor. 10.0 mL (1.00 vol) of Acetone were added, followed by a solution of 4.3 g (1.48 eq.) sodium bicarbonate and 20 mL (2.00 vol.) of purified water. The biphasic, cloudy mixture was cooled at −10 ° C., and added keeping the T below −5 ° C., with a solution of 5.0 g bis(trichloromethyl) carbonate (triphosgene, 0.49 eq.) dissolved in 20 mL of acetone (2.00 vol). The mixture was stirred at −10/-5 ° C. for at least 60 min. The reaction was then warmed to 20-25° C. and stirred 30 min. The conversion was checked by HPLC. The pH was adjusted at 7.8 by adding 13.0 g of solid sodium bicarbonate (adaptation from WO2010/032259: addition of a saturated solution required to large amount of solution, >200 mL). 80 mL (8.00 vol) of purified water were then gradually added at 20-25° C. The mixture was cooled to 10-15 ° C., stirred at least 30 min, filtered at 10-15° C. and washed with 40.0 mL (4.00 vol) of purified water. The cake was dried in vacuo at 90° C. obtaining 9.8 g of product (89.9% yield, HPLC purity 99.21% a/a, HPLC assay 96.62% wt/wt).

(According to WO2010/032259 Example 2, the product Efavirenz have a purity of 99.84%, discrepancy likely due to different analytical methods).

Example 7

Determination of ASSAY and PURITY by HPLC (Method 1—USP)

Chromatographic Conditions

| Column: | Zorbax SB-CN, 150 × 4.6 mm, 5 μm |
|---|---|
| Mobile phase A: | water/methanol/trifluoroacetic acid (TFA) 90/10/0.05 (v/v/v) |
| Mobile phase B: | Water/methanol/trifluoroacetic acid (TFA) 10/90/0.05 (v/v/v) |
| Gradient: | |

| Time (min) | % A | % B |
|---|---|---|
| 0 | 60 | 40 |
| 16 | 50 | 50 |
| 23 | 35 | 65 |
| 28 | 30 | 70 |
| 29 | 20 | 80 |
| 31 | 20 | 80 |
| 32 | 60 | 40 |
| 40 | 60 | 40 |

| Detector: | UV at 250 nm |
|---|---|
| Flow: | 1.5 mL/min* |
| Column temperature: | 40° C. |
| Injection volume: | equal volumes (about 35 μL) important note: insert washing of the needle |
| Run time: | 40 min. |
| Needle washing solution: | methanol/water (80/20) |
| Dilution solution: | acetonitrile/water (50/50) |

*The retention time of Efavirenz must be between 13 and 18 min. (about 15 min.)

Note 1:
The mobile phase must be preheated in the thermostat compartment before entering in the column to avoid the drift in the retention times and to satisfy the request of the system control referred to the retention times.

Note 2:
Before the analysis equilibrate the column for 30 minutes at the initial conditions.

Note 3:
At the end of each analysis wash the system and the column with methanol.

Preparation of the Solutions

Mobile Phase A

In a graduate cylinder mix 900 mL of water (MilliQ grade) with 100 mL of methanol and 500 μL of trifluoroacetic acid.

Do not filter mobile phase A with vacuum filter before its use, but use a degas with helium during the flow of the mobile phase, or use an "in-line membrane degasser".

Mobile Phase B

In a graduate cylinder mix 900 mL of methanol with 100 mL of water (MilliQ grade) and 500 μL of trifluoroacetic acid.

Do not filter mobile phase B with vacuum filter before its use, but use a degas with helium during the flow of the mobile phase, or use an "in-line membrane degasser".

Dilution Solution

In a graduate cylinder mix equal volumes of acetonitrile and water (MilliQ grade).

Needle Washing Solution

In a graduate cylinder mix 80 mL of methanol with 20 mL of water (MilliQ grade).

Impurities Standard Solution

Dissolve about 25 mg of each Efavirenz impurity in 75 mL of dilution solution into a 100 mL volumetric flask. Then dilute to volume with dilution solution.

Identification Standard Solution

Transfer about 25 mg of Efavirenz RS into a 100 mL volumetric flask, add about 75 mL of dilution solution and stir for 30 minutes to dissolve the sample. Add 0.5 mL of impurities standard solution, dilute to volume with dilution solution and mix well. (Solution 0.25 mg/mL of Efavirenz with 0.5% of impurities)

Working Standard Solution

In a 100 mL volumetric flask transfer about 25 mg, accurately weighed, of Efavirenz RS. Add about 75 mL of dilution solution and stir for 30 minutes to dissolve the substance. Dilute to volume with dilution solution and mix well (solution 0.25 mg/mL).

Standard Solution 0.5%

In a 100 mL volumetric flask transfer 0.5 mL, accurately measured, of working standard solution, dilute to volume with dilution solution and mix well (solution 1.25 μg/mL).

The invention claimed is:

1. A process for the preparation of Efavirenz of formula (I):

comprising the phosgenation reaction of the compound of formula (II) or salt thereof:

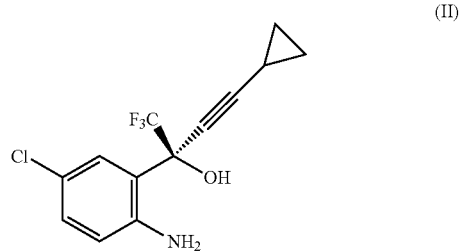 [SMILES: Nc1ccc(Cl)cc1[C@@](O)(C#CC1CC1)C(F)(F)F]

with a phosgenating agent and the reaction is performed in a biphasic system consisting of an aqueous basic or neutral phase and an organic phase, wherein the organic phase comprises a $C_{5-8}$ linear or branched or cyclic aliphatic solvent or mixtures thereof and a $C_{3-5}$ ketone solvent in the range from 30% to 70% by volume.

2. The process according to claim 1, where the volume of the organic phase is from 2.5 to 4.0 volumes with respect to the compound of formula (II).

3. The process according to claim 2, where the volume of the organic phase is from 3.0 to 3.5 volumes.

4. The process according to claim 1, wherein the $C_{3-5}$ ketone solvent is methylethylketone.

5. The process according to claim 1, wherein the aliphatic solvent is a mixture of heptanes.

6. The process according to claim 1, wherein the $C_{3-5}$ ketone solvent is methylethylketone and the aliphatic solvent is a mixture of heptanes.

7. The process according to claim 1, wherein the organic phase comprises methylethylketone in the range from 40% to 60% by volume, the rest being heptanes, and the volume of the organic phase is from 2.5 to 4.0 volumes with respect to the compound of formula (II).

8. The process according to claim 1, wherein the organic phase which comprises methylethylketone in amount of 50% by volume and 50% of heptanes and the volume of the organic phase is from 3.0 to 3.5 volumes with respect to the compound of formula (II).

9. The process according to claim 1, wherein after the quenching of the reaction and the phase separation, the organic phase is washed from 3 to 5 times with water.

10. The process according to claim 1, wherein after the quenching of the reaction and the phase separation, the washings of the organic phase with water are carried out at a temperature comprised between 40° C. and 50° C.

11. The process according to claim 1, wherein the $C_{5-8}$ linear or branched or cyclic aliphatic solvent or mixtures thereof is selected from pentane, hexane, heptane, octane, cyclohexane, cyclooctane, or cyclopentane.

* * * * *